[12] United States Patent
Goodwin

US008614165B2

(10) Patent No.: US 8,614,165 B2
(45) Date of Patent: *Dec. 24, 2013

(54) MICROORGANISM COMPOSITIONS AND METHODS

(76) Inventor: Brian B. Goodwin, Collierville, TN (US)

(*) Notice: Subject to any disclaimer, the term of this patent is extended or adjusted under 35 U.S.C. 154(b) by 107 days.

This patent is subject to a terminal disclaimer.

(21) Appl. No.: 13/183,986

(22) Filed: Jul. 15, 2011

(65) Prior Publication Data

US 2012/0015805 A1 Jan. 19, 2012

Related U.S. Application Data

(60) Provisional application No. 61/364,476, filed on Jul. 15, 2010.

(51) Int. Cl.
*A01N 25/26* (2006.01)

(52) U.S. Cl.
USPC ............ 504/100; 504/101; 504/117; 504/118

(58) Field of Classification Search
USPC .................................. 504/100, 101, 117, 118
See application file for complete search history.

(56) References Cited

U.S. PATENT DOCUMENTS

| | | | |
|---|---|---|---|
| 2,200,532 A | 12/1939 | Sherman | |
| 3,958,016 A | 5/1976 | Galle et al. | |
| 4,069,034 A | 1/1978 | Hoover | |
| 4,245,432 A | 1/1981 | Dannelly | |
| 4,249,343 A | 2/1981 | Dannelly | |
| 4,272,920 A | 6/1981 | Dawson | |
| 4,337,077 A | 6/1982 | Rutherford | |
| 4,367,609 A | 1/1983 | Lloyd | |
| 4,698,090 A | 10/1987 | Marihart | |
| 4,769,221 A | 9/1988 | Marihart | |
| 4,786,307 A | 11/1988 | Marihart | |
| 4,828,600 A | 5/1989 | McCabe et al. | |
| 4,875,921 A | 10/1989 | Paau | |
| 4,878,936 A | 11/1989 | Handelsman et al. | |
| 5,026,416 A | 6/1991 | Alexander | |
| 5,044,116 A | 9/1991 | Gago et al. | |
| 5,087,475 A | 2/1992 | Bazin et al. | |
| 5,129,180 A | 7/1992 | Stewart | |
| 5,178,661 A | 1/1993 | van der Watt et al. | |
| 5,204,368 A | 4/1993 | Cronje et al. | |
| 5,250,500 A | 10/1993 | Jones et al. | |
| 5,300,127 A | 4/1994 | Williams | |
| RE34,670 E | 7/1994 | Williams et al. | |
| 5,599,769 A | 2/1997 | Hacker et al. | |
| 5,665,671 A | 9/1997 | Zanin | |
| 5,747,020 A | 5/1998 | Rutherford et al. | |
| 5,849,320 A | 12/1998 | Turnblad et al. | |
| 5,928,997 A | 7/1999 | Bauer et al. | |
| 5,951,978 A | 9/1999 | Red'kina | |
| 6,022,744 A | 2/2000 | Tetteroo et al. | |
| 6,077,505 A | 6/2000 | Parke et al. | |
| 6,080,220 A | 6/2000 | Sequi et al. | |
| 6,080,319 A | 6/2000 | Alther | |
| 6,083,877 A | 7/2000 | Kinnersley et al. | |
| 6,090,750 A | 7/2000 | Chollet et al. | |
| 6,121,193 A | 9/2000 | Segaud et al. | |
| 6,199,318 B1 | 3/2001 | Stewart et al. | |
| 6,261,996 B1 | 7/2001 | Klittich et al. | |
| 6,277,787 B1 | 8/2001 | Malefyt et al. | |
| 6,434,884 B1 | 8/2002 | Hartung | |
| 6,453,608 B1 | 9/2002 | Flanagan et al. | |
| 6,557,298 B2 | 5/2003 | Obert et al. | |
| 6,669,849 B1 | 12/2003 | Nguyen et al. | |
| 6,698,137 B2 | 3/2004 | Muhr | |
| 6,855,536 B2 | 2/2005 | Loh et al. | |
| 6,911,415 B1 | 6/2005 | Ueland et al. | |
| 6,916,650 B2 | 7/2005 | Arndt | |
| 7,001,869 B2 | 2/2006 | Johnson | |
| 7,003,914 B2 | 2/2006 | Legro et al. | |
| 7,182,951 B1 | 2/2007 | Balachander et al. | |
| 7,213,367 B2 | 5/2007 | Wertz et al. | |
| 7,291,272 B2 | 11/2007 | Bourke et al. | |
| 7,393,678 B2 | 7/2008 | Triplett et al. | |

(Continued)

FOREIGN PATENT DOCUMENTS

| | | |
|---|---|---|
| CA | 1328238 | 4/1994 |
| CA | 2056107 | 7/1998 |
| EP | 164908 | 9/1989 |
| EP | 560943 | 3/1999 |
| EP | 949975 | 10/2002 |
| EP | 1238714 | 3/2005 |
| JP | 05-194951 A | 8/1993 |
| JP | 2008-501353 A | 1/2008 |
| WO | WO9013420 | 11/1990 |
| WO | WO9015138 | 12/1990 |

(Continued)

OTHER PUBLICATIONS

Wershaw, Robert L., "Evaluation of Conceptual Models of Natural Orgainic Matter (Humus) From a Consideration of the Chemical and Biochemical Processes of Humification", Scientific Investigations Report 2004-5121, US Department of the Interior, US Geological Survey (2004).

(Continued)

*Primary Examiner* — Rebecca Prouty
*Assistant Examiner* — Danielle Sullivan
(74) *Attorney, Agent, or Firm* — Christopher J. Knors; Moore & Van Allen PLLC

(57) ABSTRACT

Compositions comprising a first component comprising an agriculturally acceptable complex mixture of dissolved organic material characterized by natural organic matter that is partially humified and at least one agriculturally acceptable microorganism. A method comprising contacting a seed with a first component comprising an agriculturally acceptable complex mixture of dissolved organic material characterized by natural organic matter that is partially humified and at least one agriculturally acceptable microorganism, providing enhancement of at least one of nodulation, germination, emergence, root development, and nutrient uptake compared to seed not contacted with the first component or the at least one agriculturally acceptable microorganism.

31 Claims, 2 Drawing Sheets

(56) References Cited

U.S. PATENT DOCUMENTS

| | | |
|---|---|---|
| 7,510,590 B2 | 3/2009 | Anaya-Olvera |
| 7,540,965 B2 | 6/2009 | Sengupta et al. |
| 7,687,434 B2 | 3/2010 | De Billot et al. |
| 7,763,666 B2 | 7/2010 | Vero et al. |
| 7,785,474 B2 | 8/2010 | Vero et al. |
| 2002/0095864 A1 | 7/2002 | Obert et al. |
| 2002/0134012 A1 | 9/2002 | Ding et al. |
| 2003/0044382 A1 | 3/2003 | Selvig et al. |
| 2003/0130120 A1 | 7/2003 | Ziemer et al. |
| 2003/0228679 A1 | 12/2003 | Smith et al. |
| 2003/0228981 A1 | 12/2003 | Wertz et al. |
| 2004/0077498 A1 | 4/2004 | Lynch |
| 2004/0118040 A1 | 6/2004 | Asrar et al. |
| 2005/0197251 A1 | 9/2005 | Ding et al. |
| 2005/0197253 A1 | 9/2005 | Stoller et al. |
| 2006/0032120 A1 | 2/2006 | McPherson |
| 2006/0032281 A1 | 2/2006 | Meyer |
| 2006/0229203 A1 | 10/2006 | Peltonen et al. |
| 2007/0039365 A1 | 2/2007 | King et al. |
| 2007/0068072 A1 | 3/2007 | Xavier et al. |
| 2007/0074451 A1 | 4/2007 | Pearce et al. |
| 2007/0212772 A1 | 9/2007 | Hill et al. |
| 2007/0249498 A1 | 10/2007 | Van Der Drift |
| 2008/0004178 A1 | 1/2008 | Ding et al. |
| 2008/0242544 A1 | 10/2008 | Duckham et al. |
| 2008/0274885 A1 | 11/2008 | Martin et al. |
| 2009/0105076 A1 | 4/2009 | Stewart et al. |
| 2009/0105077 A1 | 4/2009 | Bhatti et al. |
| 2009/0199314 A1 | 8/2009 | Gaudillat |
| 2010/0016162 A1 | 1/2010 | Goodwin |
| 2011/0053771 A1 | 3/2011 | Goodwin |
| 2011/0078816 A1 | 3/2011 | Goodwin |
| 2011/0174031 A1 | 7/2011 | Bargiacchi et al. |

FOREIGN PATENT DOCUMENTS

| | | |
|---|---|---|
| WO | WO9210081 | 6/1992 |
| WO | WO9517806 | 7/1995 |
| WO | 01-40441 A2 | 6/2001 |
| WO | WO03020028 | 3/2003 |
| WO | WO03020837 | 3/2003 |
| WO | WO03094614 | 11/2003 |
| WO | WO2007024753 | 3/2007 |
| WO | WO2007143791 | 12/2007 |
| WO | WO2009068195 | 6/2009 |
| WO | WO2009068213 | 6/2009 |

OTHER PUBLICATIONS

Pandey, Girdhar et al., "ABR1, an APETALA2-Domain Transcription Factor that Functions as a Repressor of ABA Response in Arabidopsis", Plant Physiology, vol. 139, No. 3, pp. 1185-1193 (Nov. 2005).

http://ihss.gatech.edu/ihss2/whatarehs.html, What are Humic Substances? (Dec. 2007).

http://ihss.gatech.edu/ihss2/sources.html, Source Materials for IHSS Samples (Aug. 1, 2009).

Korean Intellectual Property Office, PCT International Search Report and Written Opinion of the International Searching Authority for International Application No. PCT/US2011/044193, dated Mar. 28, 2012.

The International Bureau of WIPO, PCT International Preliminary Report on Patentability and Written Opinion of the International Searching Authority for International Application No. PCT/US2011/044193, dated Jan. 24, 2013.

MICROORGANISM COMPOSITIONS AND METHODS

CROSS-REFERENCE TO RELATED APPLICATIONS

This application is a non-provisional application claiming benefit of Provisional Application Ser. No. 61/364,476, filed Jul. 15, 2010, the content of which is hereby incorporated in its entirety.

TECHNICAL FIELD

Disclosed are compositions and formulations comprising an agriculturally acceptable complex mixture of dissolved organic material characterized by natural organic matter that is partially humified and at least one agriculturally acceptable microorganism and methods of using the composition for seed treatments for improving at least one of nodulation, germination, emergence, root development, and nutrient uptake, and methods for reducing susceptibility of a seed or plant to disease and/or improving plant production. Specifically, the agriculturally acceptable microorganism is an inoculant, pre-inoculant, or trans-inoculant.

BACKGROUND

Various mixtures of organic compounds have been proposed in the art as fertilizer additives. Specifically, a humic acid composition, Bio-Liquid Complex™, is stated by Bio Ag Technologies International (1999) www.phelpstek.com/portfolio/humic_acid.pdf to assist in transferring micronutrients, more specifically cationic nutrients, from soil to plant.

TriFlex™ Bloom Formula nutrient composition of American Agritech is described as containing "phosphoric acid, potassium phosphate, magnesium sulfate, potassium sulfate, potassium silicate[and] sodium silicate." TriFlex™ Grow Formula 2-4-1 nutrient composition of American Agritech is described as containing "potassium nitrate, magnesium nitrate, ammonium nitrate, potassium phosphate, potassium sulfate, magnesium sulfate, potassium silicate[and] sodium silicate." Both compositions are said to be "fortified with selected vitamins, botanical tissue culture ingredients, essential amino acids, seaweed, humic acid, fulvic acid and carbohydrates." See www.horticulturesource.com/product_info.php/products_id/82. These products are said to be formulated primarily for "soilless hydrogardening" (i.e., hydroponic cultivation) of fruit and flower crops, but are also said to outperform conventional chemical fertilizers in container soil gardens. Their suitability or otherwise for foliar application as opposed to application to the hydroponic or soil growing medium is not mentioned. See www.americanagritech.com/product/product_detail.asp?ID=I &pro_id_pk=4-0.

The trademark Monarch™, owned by Actagro, LLC is a fertilizer composition containing 2-20-15 primary plant nutrients with 3% non plant food organic compositions derived from natural organic materials.

SUMMARY

There is now provided a composition comprising: a first component comprising an agriculturally acceptable complex mixture of dissolved organic material characterized by natural organic matter that is partially humified; a second component of at least one agriculturally acceptable microorganism; and at least one optional component selected from agriculturally acceptable herbicides, pesticides, fertilizers, growth regulators, and mixtures thereof.

There is now also provided a seed composition comprising: a seed; and a first component comprising an agriculturally acceptable complex mixture of dissolved organic material characterized by natural organic matter that is partially humified; a second component of at least one agriculturally acceptable microorganism; and at least one optional component selected from agriculturally acceptable sources of pesticides, fertilizers, growth regulators, and mixtures thereof.

There is still further provided a method comprising contacting a seed, foliar surface or locus of a plant with a first component comprising an agriculturally acceptable complex mixture of dissolved organic material characterized by natural organic matter that is partially humified, and a second component of at least one agriculturally acceptable microorganism, where the first and second components enhance one or more of germination, emergence, root development, yield increase, and nutrient uptake compared to the seed not contacted with the either the first or second component.

There is still further provided a method for improving nodulation, germination, growth, yield, or nutrition of a seed, comprising applying a composition comprising the first component and at least one agriculturally acceptable microorganism to a to a seed or the locus of the seed.

DETAILED DESCRIPTION

Figure 1:
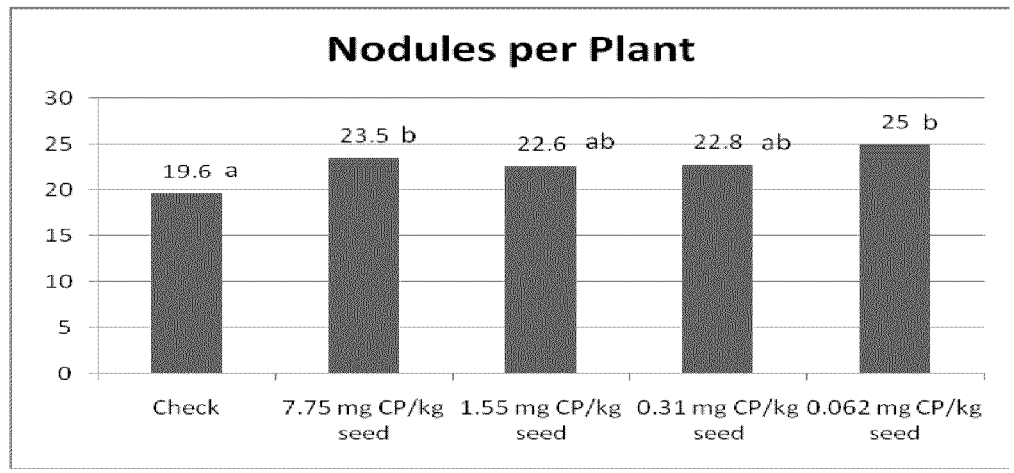
FIG. 1. graphically depicts experimental results of testing aspects of the embodiments disclosed herein.

Disclosed and described herein is, in part, seed nodulation, growth, nutrient, or health compositions and seed treatments and coatings thereof, comprising a first component comprising a natural organic material of defined composition and at least one agriculturally acceptable microorganism. In one aspect, the microorganism is an inoculant, pre-inoculant, and/or trans-inoculant. At least one optional component comprising at least one pesticide (individually or collectively, an insecticide, a fungicide, a bactericide, an anti-viral, plant nutrient, or combinations thereof) can be employed. Compositions disclosed and described herein vary depending on the intended method of application, the seed species to which they are to be applied, growing conditions of the plants, and other factors.

Compositions disclosed and described herein can take the form of aqueous solutions, oil-in-water emulsions, or water-in-oil emulsions, dispersions, seed coatings, or polymer-containing coatings.

The First Component

The first component of the composition disclosed and described herein comprises a mixture of organic molecules isolated and extracted from sources rich in natural organic matter into an aqueous solution. The natural organic matter is primarily derived from plant materials that have been modified to varying degrees over time in a soil environment. Some of the plant materials have been recently deposited in the environment. At least a part of the natural organic matter has passed through a partial process of humification to become partially humified natural organic matter. Humification includes microbial, fungal, and/or environmental (heat, pressure, sunlight, lightning, fire, etc.) degradation and/or oxidation of natural organic matter. Most preferably, the first component contains natural organic matter that has not substantially undergone humification (partially humified natural organic matter). In one aspect, the natural organic matter is obtained from environments typically containing or providing anywhere between about 5 ppm, to about 500 ppm of dissolved organic matter (DOM). In other aspects, the natural organic matter is obtained from environments typically containing or providing between about 500 ppm to about 3000 ppm or more DOM.

Natural organic matter is extremely complex, with thousands of compounds generally present, depending upon the source and the environmental conditions prevalent about the source. Humic substances such as Fulvic Acid (CAS No. 479-66-3) and Humic Acid (CAS No. 1415-93-6) are examples of organic complexes that are derived from natural organic matter, however, The first component is chemically and biologically unique from Fulvic and Humic acid, as detailed below.

The first component contains dissolved organic matter, the organic matter being formed during the process of humification as described above, such as microbial, fungicidal, and/or environmental (heat, pressure, sunlight, lightning, fire, etc.) degradation processes. Other natural or synthetic natural organic matter degradation processes may be involved or may be used. In one aspect, the first component contains predominately natural organic matter that has not undergone substantial humification (e.g., partially humified natural organic matter). The amount of humification may be determined and characterized using known methods, for example, by 13C NMR.

In one aspect, the first component is obtained by removing a natural organic matter from its source, optionally processing, and/or concentrating to provide the first component having a dissolved organic matter (DOM) concentration level of from anywhere between about 10× to about 5000× relative to its original source. In another aspect, the first component concentrations of dissolved organic matter (DOM) concentration level can be between about 7500× up to about 50,000×. The first component may be adjusted such that the concentration of DOM is between about 10 ppm to about 700,000 ppm. Preferably, the first component may be adjusted such that the concentration of DOM is between about 1000 ppm to about 500,000 ppm. The first component may be adjusted to a DOM value represented by any ppm value between 1000 ppm and 50,000 ppm, inclusive of any ppm value in 500 ppm increments (e.g., 10,500 ppm, 11,000 ppm, 11,500 ppm, 12,000 ppm, etc.) in aqueous solution. Other DOM concentrations may be used, for example, an extremely concentrated composition of between about 75,000 ppm and about 750,000 ppm can be prepared. For example, a concentrate of about 30,000× of the original source can contain about 550,000 ppm of DOM. In certain aspects, the first component are approximately between about 91% to about 99% water, the remaining organic material being primarily DOM with minor amounts of alkali-, alkali earth-, and transition metal salts. In yet other aspects, the DOM of the first component has been dried or lyophilized in a form suitable for reconstitution with an aqueous solution.

The first component is a complex mixture of substances, typically a heterogeneous mixture of compounds for which no single structural formula will suffice. Elemental and spectroscopic characterization of the first component differentiates it from most other humic-based organic complexes, such as Humic and Fulvic Acids, as further discussed below. Blending of individual batches of the first component may be performed to provide consistency and to compensate for the normal variations of a naturally-derived material.

Detailed chemical and biological testing has shown that the complex mixture of substances of the first component is a unique composition both in its biological effect on plants and its chemical composition compared to Humic and Fulvic acids.

Characterization and Methods for the First Component

The organic compounds making up the first component of the composition, can be characterized in a variety of ways (e.g., by molecular weight, distribution of carbon among different functional groups, relative elemental composition, amino acid content, carbohydrate content, etc.). In one aspect, the first component was characterized relative to known standards of humic-based substances.

For purposes of characterizing carbon distribution among different functional groups, suitable techniques include, without limitation, 13C-NMR, elemental analysis, Fourier transform ion cyclotron resonance mass spectroscopy (FTICR-MS) and Fourier transform infrared spectroscopy (FTIR). The chemical characterization of the first component and Humic substance standards were carried out using Electro spray Ionization Fourier Transform Ion Cyclotron Resonance Mass Spectroscopy (ESI-FTICR-MS), Fourier Transform Infrared Spectroscopy (FTIR) and elemental analysis for metals using ICP-AES, conducted by Huffman Laboratories, Inc. and the University of Washington.

Elemental, molecular weight, and spectroscopic characterization of the first component is consistent with an organic complex that consists primarily of lignin and tannin compounds (and mixtures of condensed and un-condensed tannin), condensed aromatics and trace amounts of lipid and inorganics. Thousands of compounds are present, with molecular weights ranging from 225 to 700 daltons, the majority of compounds having between about 10 to about 39 carbon atoms per molecule. The first component is generally composed of carbon, oxygen, and hydrogen, with small amounts of nitrogen, and sulfur. The first component also contains potassium and iron at levels above 5%.

The elemental composition of the dissolved solids typically present in the first component is given in Table A. If the organic compounds are separated from the inorganic elements, the elemental breakdown is: C 55%, H 4%, O 38%, N 1.8%, and S 2.2%.

TABLE A

Average Elemental Composition of dissolved solids in the first component, based upon average values from 10 different lots.

| Element | % |
| --- | --- |
| Carbon | 35.1 |
| Oxygen | 24.6 |
| Hydrogen | 2.5 |
| Sulfur | 2.1 |
| Nitrogen | 1.3 |
| Potassium | 27.3 |
| Iron | 6.1 |
| Calcium | 0.2 |
| Sodium | 0.2 |
| Phosphorous | 0.1 |
| Other | 0.5 |

Among the classes of organic compounds present in the first component, preliminary analysis generally revealed that there are lignin and tannin (mixture of condensed and un-condensed), condensed aromatics, unidentified substances and some lipids present. Each of these classes of compounds is further characterized by a rather narrow Mw range and number of carbons/molecule. The breakdown of the number and percentage of each of the various compound classes, their MW's and carbon atoms/molecule (Carbon Range) for a first representative sampling of the first component is given in Table B1.

TABLE B1

Compound Classes in the first component, along with size and carbon ranges for compounds in each class. Based upon composite of 3 different production batches. Results for individual batches are very similar.

| Compound Class | # Compounds | % of Total | Size Range (daltons) | Carbon Range |
|---|---|---|---|---|
| Lignin | 1139 | 57 | 226-700 | 11 to 39 |
| Tannin | 587 | 30 | 226-700 | 10 to 31 |
| Condensed Aromatic | 220 | 11 | 238-698 | 13 to 37 |
| Lipid | 18 | 1 | 226-480 | 14 to 30 |
| Carbohydrate | 1 | 0 | 653 | 24 |
| Other | 23 | 1 | 241-651 | 12 to 33 |

A breakdown of the number and percentage of each of the various compound classes, their MW's and carbon atoms/molecule (Carbon Range) for a second representative sampling based upon an average of 3 different production batches for the first component is given in Table B2.

TABLE B2

Compound Classes in the first component, along with size and carbon ranges for compounds in each class. Based upon average of 3 different production batches. Results for individual batches are very similar.

| Compound Class | # Compounds | % of Total | Size Range (daltons) | Carbon Range |
|---|---|---|---|---|
| Lignin | 711 | 56 | 226-700 | 11 to 39 |
| Tannin | 410 | 33 | 226-700 | 10 to 31 |
| Condensed Aromatic | 122 | 10 | 238-698 | 13 to 37 |
| Lipid | 12 | ~1 | 226-480 | 14 to 30 |
| Carbohydrate | 1 | 0 | 653 | 24 |
| Other | 14 | ~1 | 241-651 | 12 to 33 |

Table C, summarizes the oxygen-to-carbon (O/C) and hydrogen-to-carbon (H/C) ratios used in defining the classes described above.

TABLE C

Elemental Ratios and chemical classifications used in characterizing samples of the first component.

| Class | O/C | H/C | Aromaticity Index |
|---|---|---|---|
| Lignin | 0.15-0.6 | 0.6-1.7 | <0.7 |
| Tannin | 0.6-1.0 | 0.5-1.4 | <0.7 |
| Condensed Aromatic | 0.1-0.7 | 0.3-0.7 | >0.7 |
| Lipid | 0-0.2 | 1.8-2.2 | |
| Carbohydrate | 0.6-1.0 | 1.8-2.2 | |

Comparison with Humic Substance Standards

Comparative elemental and structural characterization of Humic Substances verses samples of the first component were performed. Three humic substances standards from the International Humic Substances Society were used: Leonardite Humic Acid (LHA), Pahokee Peat Humic Acid (PPHA), and Suwannee River Fulvic Acid II (SRFA). Each humic substance standards and each sample of the first component was analyzed by FTIR and ESI-FTICR-MS. A portion of each humic substance standard was dissolved in $NH_4OH$/water for the ESI-FTICR-MS analysis. Three samples of the first component (#1, #2, and #3) were prepared for analysis with cation exchange resin (AG MP-50, Bio-Rad Laboratories, Hercules, Calif.). Comparison of the Humic Substance standards and each sample of the first component is presented in Table D.

TABLE D

Comparison of humic substance standards samples of the first component.

| Sample | O/C | H/C | DBE | Avg. MW |
|---|---|---|---|---|
| Suwannee River Fulvic Acid (SRFA) | 0.39 | 1.01 | 12.7 | 445.7 |
| Pahokee Peat Humic Acid (PPHA) | 0.34 | 0.75 | 16.29 | 429.8 |
| Leonardite Humic Acid (LHA) | 0.3 | 0.79 | 15.8 | 423.6 |
| #1 | 0.54 | 0.87 | 13.7 | 472.9 |
| #2 | 0.54 | 0.89 | 13.23 | 456.9 |
| #3 | 0.5 | 0.91 | 13.23 | 455.7 |

Table D indicates that there are major differences between the Humic Substances standards and the samples representing the first component. For example, the O/C ratio is less than 0.4 in all of the Humic Substances but is at least 0.5 for the first component samples. The DBE for the samples is also significantly lower than for the Humic Acid Standards and the average MW is greater.

Based on mass spectral analysis, there are a number of compounds present in the first component samples that are substantially absent or greatly reduced in the Humic Substance standards. In particular, at least one component of the first component may correspond with one or more tannin compounds. By comparison, in the Humic Substance standards, the % of tannin compounds are present in a small amount. For example, in the Fulvic Acid standard and in the Humic Acid standards, both standards are at least 3×-4× less than the % tannins found in the first component samples, as shown in Table E.

TABLE E

Number and % tannins in Humic Substance Standards verses first component samples.

| Sample | # tannins | % of tannin compounds |
|---|---|---|
| Suwannee River Fulvic Acid (SRFA) | 192 | 8.8 |
| Pahokee Peat Humic Acid (PPHA) | 9 | 1.2 |
| Leonardite Humic Acid (LHA) | 22 | 1.2 |
| #1 | 441 | 35.2 |
| #2 | 357 | 34.6 |
| #3 | 432 | 28.3 |

Comparing the Fourier Transform Infrared (FTIR) spectra for the IHSS standards and first component samples, there are similarities, primarily in the region from 1600 to 1800 $cm^{-1}$. In both sets of samples we see a very strong peak at around 1700 $cm^{-1}$ due to the C=O stretch from a carboxyl functional group and a peak in the 1590 to 1630 region which is consistent with a C=C bond from alkenes or aromatics. However, significant differences in the region from 700 to 1450 $cm^{-1}$ are observed. Peaks at 1160 to 1210 are present in all the spectra and are from the C—O bond of alcohols, ethers, esters and acids. The biggest difference is the peak at 870 $cm^{-1}$ in the first component samples, which is absent in the IHSS standards. This peak may be due to the C—H bond of alkenes and aromatics.

Based on the characterization data, the first component may contain relatively small molecules or supramolecular aggregates with a molecular weight distribution of about 300 to about 18,000 daltons. Included in the organic matter from which the mixture of organic molecules are fractionated are various humic substances, organic acids and microbial exudates. The mixture is shown to have both aliphatic and aromatic characteristics. Illustratively, the carbon distribution shows about 35% in carbonyl and carboxyl groups; about 30% in aromatic groups; about 18% in aliphatic groups, about 7% in acetal groups; and about 12% in other heteroaliphatic groups.

In some embodiments, the mixture of compounds in the first component comprises organic molecules or supramolecular aggregates with a molecular weight distribution of about 300 to about 30,000 daltons, for example, about 300 to about 25,000 daltons, about 300 to about 20,000 daltons, or about 300 to about 18,000 daltons.

Characterizing carbon distribution among different functional groups, suitable techniques can be used include without limitation 13C-NMR, elemental analysis, Fourier transform ion cyclotron resonance mass spectroscopy (FTICR-MS) and Fourier transform infrared spectroscopy (FTIR).

In one aspect, carboxy and carbonyl groups together account for about 25% to about 40%, for example about 30% to about 37%, illustratively about 35%, of carbon atoms in the mixture of organic compounds of the first component.

In one embodiment, aromatic groups account for about 20% to about 45%, for example about 25% to about 40% or about 27% to about 35%, illustratively about 30%, of carbon atoms in the mixture of organic compounds of the first component.

In one embodiment, aliphatic groups account for about 10% to about 30%, for example about 13% to about 26% or about 15% to about 22%, illustratively about 18%, of carbon atoms in the mixture of organic compounds of the first component.

In one embodiment, acetal and other heteroaliphatic groups account for about 10% to about 30%, for example about 13% to about 26% or about 15% to about 22%, illustratively about 19%, of carbon atoms in the mixture of organic compounds of the first component.

In one aspect, the ratio of aromatic to aliphatic carbon is about 2:3 to about 4:1, for example about 1:1 to about 3:1 or about 3:2 to about 2:1 in the first component.

In a particular illustrative aspect, carbon distribution in the mixture of organic compounds of the first component is as follows: carboxy and carbonyl groups, about 35%; aromatic groups, about 30%; aliphatic groups, about 18%, acetal groups, about 7%; and other heteroaliphatic groups, about 12%.

Elemental composition of the organic compounds of the first component is independently in one series of embodiments as follows: by weight: C, about 28% to about 55%, illustratively about 38%; H, about 3% to about 5%, illustratively about 4%; O, about 30% to about 50%, illustratively about 40%; N, about 0.2% to about 3%, illustratively about 1.5%; S, about 0.2% to about 4%, illustratively about 2%.

Elemental composition of the organic compounds of the first component is independently in another series of embodiments as follows, by weight: C, about 45% to about 55%, illustratively about 50%; H, about 3% to about 5%, illustratively about 4%; O, about 40% to about 50%, illustratively about 45%; N, about 0.2% to about 1%, illustratively about 0.5%; S, about 0.2% to about 0.7%, illustratively about 0.4%.

In a particular illustrative aspect, elemental distribution is, by weight: C, about 38%; H, about 4%; O, about 40%; N, about 1.5%; and S, about 2%. The balance consists mainly of inorganic ions, principally potassium and iron in the first component.

In another particular illustrative aspect, elemental distribution is, by weight: C, about 50%; H, about 4%; O, about 45%; N, about 0.5%; and S, about 0.4% in the first component.

Among classes of organic compounds that can be present in the first component are, in various aspects, amino acids, carbohydrates (monosaccharides, disaccharides and polysaccharides), sugar alcohols, carbonyl compounds, polyamines, lipids, and mixtures thereof. These specific compounds typically are present in minor amounts, for example, less than 5% of the total % of compounds.

Examples of amino acids that can be present include without limitation arginine, aspartic acid, glutamic acid, glycine, histidine, isoleucine, serine, threonine, tyrosine and valine.

Examples of monosaccharide and disaccharide sugars that can be present include without limitation glucose, galactose, mannose, fructose, arabinose, ribose and xylose.

Based on the above chemical, elemental and structural characterization, the first component is chemically and biologically unique from Humic and Fulvic acids or combinations thereof. Further, as a result of the nature and extent of gene regulation and over all effect of the first component with respect to improved plant health, drought and salinity stress resistance, it is generally believed that the first component is unique to that of known humic and/or fulvic acid compositions and treatments, for which such activity and properties are generally lacking in quality and quantity. Other beneficial plant function attributes of the first component may be present or result from the methods of treatment and/or the gene regulation obtained from the first component.

Without being bound by theory, it is believed that at least the ability of the first component to complex ions assists in plant nutrition by facilitating uptake and/or translocation of ions in the plant. Facilitating uptake and/or translocation of ions may occur through preferential movement of ions via the xylem or phloem to the growing and fruiting points of the plant. Alternatively, or in combination with the above, facilitating uptake and/or translocation of ions may occur through regulation of one or more genes related to ion transport or other biological function of the plant or seed. Facilitating uptake and/or translocation of ions may occur through absorption and transport via the seed coat of the pre- or post-planted seed. Inorganic ions can be positively charged cations or negatively charged anions. Examples of inorganic cations include $Mg^{2+}$, $Ca^{2+}$, $Mn^{2+}$, $Fe^{2+}$ and $Fe^{3+}$. Examples of inorganic anions include borate and silicate Such reversible binding or complexing may take the form of chelation or by ionic or non-ionic interaction. Other abilities of the first component to assists in plant nutrition can be present or employed.

A suitable mixture of organic compounds can be found in products marketed as Carbon Boost-S soil solution and KAFE™-F foliar solution of Floratine Biosciences, Inc. (FBS), the active ingredient having CAS Reg. No. 1175006-56-0, and corresponding, by way of example, to the first component. Information on these products is available at www.fbsciences.com. Thus, exemplary compositions of aspects disclosed and described herein can be prepared by adding to Carbon Boost™-S or KAFE™-F foliar solution as the first component, at least one microorganism and optionally, at least one pesticide.

The amount of the first component that should be present in the composition depends on the particular organic mixture used. The amount should not be so great as to result in a physically unstable composition, for example by exceeding the limit of solubility of the mixture in the composition, or by causing other essential components to fall out of solution. On the other hand, the amount should not be so little as to fail to provide enhanced nodulation, emergence, root development, nutrition, growth, enhanced stress resistance, or enhanced disease protection when applied to a target plant species. For any particular organic mixture, one of skill in the art can, by routine formulation stability and bioefficacy testing, optimize the amount of organic mixture in the composition for any particular use.

Particularly where a mixture of organic compounds, as found, for example, in the commercially available formulations sold under the tradenames Carbon Boost™-S and KAFE™-F, is used, the amount of the first component needed in a nutrition composition will often be found to be remarkably small. For example, as little as one part by weight (excluding water) of such a mixture can, in some circumstances, assist in foliar delivery of up to about 1000 or more parts by weight of the second component to a site of deposition in a plant. In other circumstances, it may be found beneficial to add a greater amount of the organic mixture, based on routine testing. Typically, a suitable ratio of the first component to the second component is about 1:2000 to about 1:5, for example about 1:1000 to about 1:10 or about 1:500 to about 1:20, illustratively about 1:100. If using Carbon Boost™-S or KAFE™-F solution as the source of organic compounds, a suitable amount of such solution to be included in a concentrate composition of second component herein is about 1 part by weight Carbon Boost™-S or KAFE™-F solution in about 5 to about 25, for example about 8 to about 18, illustratively about 12, parts by weight of the concentrate composition.

Optionally, additional components can be present in a composition of the present disclosure together with the first component and microorganism as describe above. For example, the composition can further comprise as an optional component, at least one agriculturally acceptable pesticide. Additional sources of these nutrients can be present, if desired.) Examples of other plant nutrients, sources of which can optionally be included, are potassium (K), and sulfur (S), phosphorus (P), calcium (Ca), magnesium (Mg), iron (Fe), zinc (Zn), manganese (Mn), copper (Cu) and boron (B).

Advantageously, addition of multivalent cations such as $Ca^{+2}$, $Mg^{+2}$, $Mn^{+2}$, or $Fe^{+2/3}$ to an aqueous composition containing the first component, microorganism with pesticides that are generally know to complex with the multivalent cations such as Ca, Mg, Mn, or Fe can substantially maintain the potency of the pesticide compared to a solution comprising the multivalent cations and pesticide in the absence of the first component.

Other ingredients can optionally be present in a composition disclosed and described herein, including such conventional formulation adjuvants as surfactants (for example to enhance wetting of seed or foliar surfaces), antifoam agents, spray drift controlling agents, viscosity modulating agents, antifreezes, coloring agents, penetrates, etc. Any of these can be added if desired, so long as they do not destabilize essential components of the composition.

Processes for preparing a composition disclosed and described herein typically involve simple admixture of the required ingredients. If desired, any of the ingredients can be pre-dissolved in a suitable volume of water before mixing with other ingredients. Order of addition is not generally critical.

Microorganisms

In one aspect, the microorganism comprises at least one of an inoculants, trans-inoculants, or pre-inoculants useful in combination with the first component, and can include, for example, nitrogen-fixing bacteria, phosphate-solubilizing bacteria, fungal inoculants, and composite inoculants. Unless stated otherwise, reference to an inoculant is inclusive of all known members of the stated inoculants taxonomic classification that are capable of inoculating or pre-inoculating seed. Various microorganisms have beneficial effects on plants, for example *Rhizobium, Bradyrhizobium, Bacillus, Azobacter, Arhrobacter, Pseudomonas, Azospirillium, cyanobacteria*, and *mycorrihizal fungae*. While specific emphasis is noted for the combination of the first component with *Rhizobium*, similar principles of combination apply to the other microoganisms, some of which are disclosed below without limitation thereof. In some aspects, the inoculant can include other microorganisms that do not provide any agronomic benefit.

Inoculants can include bacterial strains *Herbaspirillum seropedicae* 2A, *Pantoea agglomerans* P101, *Pantoea agglomerans* P102, *Klebsiella pneumoniae* 342, *Klebsiella pneumoniae zmvsy, Herbaspirillum seropedicae* Z152, *Gluconacetobacter diazotrophicus* PA15, with or without a carrier. The inoculant can also include strains of the bacterium *Pantoea agglomerans* and *K. pneumoniae* which are able to enhance the growth of cereal grasses. Bacterial strains of *Herbaspirillum seropedicae* 2A, *Pantoea agglomerans* P101 and P102, and *Klebsiella pneumoniae* 342 and *zmvsy* can also be used.

Examples of nitrogen-fixing bacteria inoculants include rhizobacteria, for example, *Rhizobium japonicum* and *Bradyrhizobium japanicum* and closely related genera. Genetically modified *Rhizobium*, such as trifolitoxin expressing types, are examples of trans-inoculants. Nitrogen-fixing bacteria in combination with the first component is useful for non-leguminous crops, for example, *Azospirillum*, and diazotrophic rhizobacteria for cereal crops.

*Bradyrhizobium* species specifically include the commercially important soybean nodulating strains *B. japonicum* (i.e., strains USDA 110 and 123), promiscuous rhizobia of the cowpea group, and *B. parasponia* (formerly *Parasponia rhizobium*) which nodulates the non-legume Parasponia, as well as a number of tropical legumes, including cowpea and siratro. An important agricultural host of *B. japonicum* is soybean (*Glycine max*), but this bacterium will nodulate a few other legumes (e.g., cowpea and siratro). Fast growing rhizobia include, among others, *Rhizobium etli, Sinorhizobium meliloti* (formerly *Rhizobium meliloti*), and *Rhizobium leguminosarum biovar trifolii*, which nodulate bean, alfalfa, and clover, respectively. *Rhizobium* sp. NGR234, for example, has been shown to nodulate over 100 genera of legumes. *Sinorhizobium fredii* (formerly *Rhizobium fredii*), is phylogenetically distinct from *B. japonicum*, but has the ability to nodulate *Glycine soja* (a wild soybean species), *G. max* cv. Peking, and a few other soybean cultivars. High-yielding NolA insensitive *B. japonicum* and nolA inducers can be employed for situations involving inefficient nodulation due to indigenous *B. japonicum* strains.

Certain soil bacteria, such as Gram negative strains including *Pantoea agglomerans* and related diazotrophs, are useful for stimulating nodulation in legumes and perhaps limit growth of phytopathogenic fungi. Other bacterial strains include *Burkholderia cepacia* 2J6 (ATCC Accession No. 55982), *Burkholderia cepacia* AMMD 2358 (ATCC Accession No. 55983) and *Azospirillum brasilense* SAB MKB having accession number NRRL B-30081. Other examples of soil bacteria include, for example, *Bacillus subtilis*, known as the hay bacillus or grass bacillus, a Gram-positive, catalase-positive bacterium, *Bacillus pumilus* (e.g., strain GB34) useful for protecting the roots of the soybean plant against certain fungi.

Examples of phosphate-solubilizing bacteria include, for example, *Agrobacter radiobacter*.

Examples of fungal inoculants include, for example, vesicular-arbuscular mycorrhizae (VAM), arbuscular mycorrhizae (AM), *Penicillium bilaii*, and endophytic fungi, such as *Piriformis indica*. Other fungal inoculants can include, for example, members of the *Trichoderma* genus of fungi characterized as opportunistic avirulent plant symbionts effective against fungal diseases of root surfaces, e.g., the species *T. harzianum*, *T. viride* and *T. hamatum*

Specific combinations envisaged include, for example, *Penicillium bilaii* and *Rhizobium* spp (inclusive of *Rhizobium* genus and *Bradyrhizobium* genus).

Examples of composite inoculants include, for example, the combination of strains of plant growth promoting Rhizobacteria (PGPR) and arbuscular mycorrhizae, or multiple strain inoculants where only one strain is diazotrophic.

Examples of legume classes suitable for use with the compositions disclosed herein include, but are not limited to grain legumes such as various varieties of beans, lentils, lupins, peas, and peanuts, soybean, and peas. Exemplary, non-limiting examples include American groundnut, azuki bean, black bean, black-eyed pea, chickpea (garbanzo bean), drumstick, dolichos bean, fava bean (broad bean), French bean, guar, haricot bean, horse gram, Indian pea, kidney bean, lentil, lima bean, moth bean, mung bean, navy bean, okra, pea, peanut (groundnut), pigeon pea, pinto bean, rice bean, runner bean, soybean, tarwi, tepary bean, urad bean, velvet bean, winged bean and yardlong bean, and industrial legumes of the *Indigofera* and *Acacia* species. Other exemplary legumes suitable for the formulations and compositions disclosed herein include, for example, Pink Beans, Green Baby Lima, Chickpea Café Type, Dark Red Kidney Beans, Black Beans, Small red Beans, Cranberry Beans Great Northern bean Small Red, Milky White, Pedrosillano, Athena, Beluga, Crimson, Crimson Decorticated, Eston, French Green, Pardina, Red Chief, Red Chief Decortcated, Richle,a Large Green, Regular, Austrian Winter, Whole Green, Green Split, Marrowfat, Whole Yelow, and Yelow Split. Forage legumes, such as alfalfa, Alsike Clover, Arrowleaf Clover, Berseem Clover, Birdsfoot Trefoil, Cicer Milkvetch, Crimson Clover, Hairy Vetch, Kura Clover, Ladino Clover, Mammoth Red Clover, Medium Red Clover, Sainfoin, Strawberry Clover, White Clover, and Yellow Blossom Sweet Clover. Fallow/green manure legume species, such as, *Leucaena, Cyamopsis*, and *Sesbania* species. Other legume species include the numerous *Acacia* species and *Castanospermum australe*.

The inoculant can be applied in a liquid composition, for example, physically mixed or blended with an aqueous solution comprising the first component to result in a formulation suitable for seed treating. The seed can be sequentially treated, for example, with the first component followed by the inoculant, for example, immediately thereafter or after a predetermined time or arbitrary time period has elapsed. The inoculant can also be provided in a solid or semi-solid state, which can include a carrier, such as peat, irradiated sedge peat in particular. Additional agents can be used, including for example, adhesion agents, water-insoluble and/or water soluble polymers conventionally used in the dispensing and application of inoculants to seeds.

Optional Pesticide

An optional component can be employed, which can be at least one of a pesticide, where the term "pesticide" herein refers to at least one of a herbicide, an insecticide, a fungicide, a bactericide, an anti-viral, a plant nutrient, or a combination thereof.

Herbicides in general are not applied to seeds or combined together with inoculants and compositions such as the first component, however it is nonetheless possible to include, for example, any herbicide that is effective for the control or remediation of incidental weed seed present in the locus of the intended sowing, for example imidazolinone, sulfonylurea, glyphosate, glufosinate, L-phosphinothricin, triazine, benzonitrile and combinations thereof. Herbicides also include Dicamba (3,6-dichloro-o-anisic acid or 3,6-dichloro-2-methoxybenzoic acid), the active ingredient in herbicides such as Banvel™, (BASF), Clarity™, (BASF), and Vanquish™ (Syngenta). Coatings of a sequential construction, whereas the herbicide is applied as the last component, and/or buffered from the first component and/or microorganism can be used.

Insecticides can include, for example, any insecticide that is effective for the control or remediation of insects, and include ovicides and larvicides. Exemplary insecticides include organochlorines, organophosphates, carbamates, neonicotinoids, phenylpyrazoles, and pyrethroids, for example tefluthrin, terbufos, cypermethrin, thiodicarb, lindane, furathiocarb, acephate, butocarboxim, carbofuran, NTN, endosulfan, fipronil, diethion, aldoxycarb, methiocarb, oftanol, (isofenphos), chlorpyrifos, bendiocarb, benfuracarb, oxamyl, parathion, capfos, dimethoate, fonofos, chlorfenvinphos, cartap, fenthion, fenitrothion, HCH, deltamethrin, malathion, disulfoton, clothianidin, and combinations thereof. In one aspect, the pesticide comprises an insecticidally effective amount of at least one neonicotinoid or phenylpyrazole insecticide, and combinations thereof.

Fungicides in general are not combined with inoculants and applied together to seeds, such as soybean. However, it is nonetheless possible to combine the inoculant with certain fungicidal mixtures such as Mefenoxam & Fludioxonil (ApronMaxx RTA, Syngenta USA) in combination with the first component with seeds, for example, soy beans and other. Other fungicides and fungicidal mixtures can also be used in combination with the first component provided that the effect of the fungicide on the inoculant is minimal. In certain aspects, the pesticide together with or separately from the first component is applied sequentially, before or after application of the inoculant.

Anti-viral agents can include, for example, agents that are effective for the control or remediation of asymptomatic viruses, nematodes protozoa and parasitic plants in combination with the first component provided that the effect of the fungicide on the inoculant is minimal.

The optional component can also include growth regulators, for example, cytokinins, auxins, gibberellins, and combinations thereof with any of the compounds listed above.

The optional component can also comprise one or more plant macronutrients or plant micronutrients. The term "macronutrient" can refer to an element for plant growth which is utilized by plants in proportionally larger amounts relative to micronutrients. The term "micronutrients" refers to an element utilized by plants during growth which are used in smaller amounts relative to macronutrients. For example, plant macronutrients include nitrogen, potassium, phosphorus, calcium, magnesium and sulfur. The optional component can comprise various combinations and relative amounts of individual macronutrients. For example, plant micronutrients include iron, manganese, zinc, copper, boron, molybdenum and cobalt. Numerous compounds and substances are available to provide micronutrients as the optional component. Various combinations and relative amounts of micronutrients can be utilized in the optional component. The optional component can also include, in addition to any of the above, a mold inhibitor, an absorbent, a penetrant, and combinations thereof.

Methods

Methods of use of the composition as described herein for seed treating, nodule formation, germination, emergence, root development, nutrition, and/or for reducing susceptibility to disease of a seed, are further disclosed and provided. The composition can be applied to a single seed or to an assemblage of seeds in bulk or in a continuous process. In some embodiments, the composition is applied to an agricultural or horticultural seed, more especially a food crop. A "food crop" herein means a crop grown primarily for human consumption. Methods disclosed herein are appropriate both for immediately prior to sowing or for stored seed.

While the present methods can be beneficial for gramineous (belonging to the grass family) crops such as cereal crops, including corn, wheat, barley, oats, rye, triticale, and rice, they are also highly appropriate for non-gramineous crops, including vegetable crops, fruit crops and seed crops. The terms "fruit" and "vegetable" herein are used in their agricultural or culinary sense, not in a strict botanical sense; for example, tomatoes, cucumbers and zucchini are considered vegetables for present purposes, although botanically speaking it is the fruit of these crops that is consumed. Vegetable crops for which the present methods can be found useful include without limitation:

leafy and salad vegetables such as amaranth, beet greens, bitterleaf, bok choy, Brussels sprout, cabbage, catsear, celtuce, choukwee, Ceylon spinach, chicory, Chinese mallow, chrysanthemum leaf, corn salad, cress, dandelion, endive, epazote, fat hen, fiddlehead, fluted pumpkin, golden samphire, Good King Henry, ice plant, jambu, kai-lan, kale, komatsuna, kuka, Lagos bologi, land cress, lettuce, lizard's tail, melokhia, mizuna greens, mustard, Chinese cabbage, New Zealand spinach, orache, pea leaf, polk, radicchio, rocket (arugula), samphire, sea beet, seakale, Sierra Leone bologi, soko, sorrel, spinach, summer purslane, Swiss chard, tatsoi, turnip greens, watercress, water spinach, winter purslane and you choy;

flowering and fruiting vegetables such as acorn squash, Armenian cucumber, avocado, bell pepper, bitter melon, butternut squash, caigua, Cape gooseberry, cayenne pepper, chayote, chili pepper, cucumber, eggplant (aubergine), globe artichoke, luffa, Malabar gourd, parwal, pattypan squash, perennial cucumber, pumpkin, snake gourd, squash (marrow), sweetcorn, sweet pepper, tinda, tomato, tomatillo, winter melon, West Indian gherkin and zucchini (courgette);

podded vegetables (legumes) such as American groundnut, azuki bean, black bean, black-eyed pea, chickpea (garbanzo bean), drumstick, dolichos bean, fava bean (broad bean), French bean, guar, haricot bean, horse gram, Indian pea, kidney bean, lentil, lima bean, moth bean, mung bean, navy bean, okra, pea, peanut (groundnut), pigeon pea, pinto bean, rice bean, runner bean, soybean, tarwi, tepary bean, urad bean, velvet bean, winged bean and yardlong bean;

bulb and stem vegetables such as asparagus, cardoon, celeriac, celery, elephant garlic, fennel, garlic, kohlrabi, kurrat, leek, lotus root, nopal, onion, Prussian asparagus, shallot, Welsh onion and wild leek;

root and tuber vegetables, such as ahipa, arracacha, bamboo shoot, beetroot, black cumin, burdock, broadleaf arrowhead, camas, canna, carrot, cassava, Chinese artichoke, daikon, earthnut pea, elephant-foot yam, ensete, ginger, gobo, Hamburg parsley, horseradish, Jerusalem artichoke, jicama, parsnip, pignut, plectranthus, potato, prairie turnip, radish, rutabaga (swede), salsify, scorzonera, skirret, sweet potato, taro, ti, tigernut, turnip, ulluco, wasabi, water chestnut, yacon and yam; and herbs, such as angelica, anise, basil, bergamot, caraway, cardamom, chamomile, chives, cilantro, coriander, dill, fennel, ginseng, jasmine, lavender, lemon balm, lemon basil, lemongrass, marjoram, mint, oregano, parsley, poppy, saffron, sage, star anise, tarragon, thyme, turmeric and vanilla.

Fruit crops for which the present methods can be found useful include without limitation apple, apricot, banana, blackberry, blackcurrant, blueberry, boysenberry, cantaloupe, cherry, citron, clementine, cranberry, damson, dragonfruit, fig, grape, grapefruit, greengage, gooseberry, guava, honeydew, jackfruit, key lime, kiwifruit, kumquat, lemon, lime, loganberry, longan, loquat, mandarin, mango, mangosteen, melon, muskmelon, orange, papaya, peach, pear, persimmon, pineapple, plantain, plum, pomelo, prickly pear, quince, raspberry, redcurrant, starfruit, strawberry, tangelo, tangerine, tayberry, ugli fruit and watermelon.

Seed crops, for example, specialized crops used to produce seed of any plant species, for which the present methods can be found useful include, in addition to cereals (e.g., barley, corn (maize), millet, oats, rice, rye, sorghum (milo) and wheat), non-gramineous seed crops such as buckwheat, cotton, flaxseed (linseed), mustard, poppy, rapeseed (including canola), safflower, sesame and sunflower.

Other crops, not fitting any of the above categories, for which the present methods can be found useful include without limitation sugar beet, sugar cane, hops and tobacco.

Each of the crops listed above has its own particular nutrition and disease protection needs. Further optimization of compositions described herein for particular crops can readily be undertaken by those of skill in the art, based on the present disclosure, without undue experimentation.

Methods of using the compositions disclosed and described herein comprise applying a composition as described herein to a seed, or to a locus of the seed.

The term "agriculturally acceptable" applied to a material or composition herein means not unacceptably damaging or toxic to a plant or its environment, and not unsafe to the user or others that may be exposed to the material when used as described herein.

A "foliar surface" herein is typically a leaf surface, but other green parts of plants have surfaces that may permit absorption of active ingredient, including petioles, stipules, stems, bracts, flowerbuds, etc., and for present purposes, "foliar surfaces" will be understood to include surfaces of such green parts.

A "locus" as used herein-includes an area in proximity to a seed or the area in which a plurality of seed is or can be sown and includes root parts and husk of seeds.

"Seed treatment" as used herein refers generally to contacting a seed with a compound or composition of matter containing or comprising at least one active ingredient (a.i. or AI). The compound or composition of matter may be in any form suitable to the seed, for example, liquid, spray or powder. Seed treatment is inclusive of seed coating and seed dressing.

"Seed coating" or "seed dressing" as used herein refers generally to a coating or matrix formed on at least part of the seed, the coating or matrix containing or comprising the at least one AI. Optional compounds or agents may be included in the seed coating to facilitate the seed coating process or the disintegration/releasing of the at least one AI from the coating, or to prevent excessive dust-off or to add color to the treated seed.

The term "seed" as used herein, is not limited to any particular type of seed and can refer to seed from a single plant species, a mixture of seed from multiple plant species, or a seed blend from various strains within a plant species. The disclosed and described compositions can be utilized to treat gymnosperm seed, dicotyledonous angiosperm seed and monocotyledonous angiosperm seed.

In another particular aspect, an effective seed treatment comprises a seed treated with a combination comprising the first component and the at least one agriculturally acceptable microorganism, an optional component comprising a plant growth hormone. The plant growth hormone can be from the class of abscisic acid, auxins, cytokinins, gibberellins, brassinolides, salicyclic acid, jasmonates, plant peptides, polyamines, and stringolactones.

Compositions disclosed and described herein can be provided in concentrate form, (e.g., liquid, gel, or reconstitutable powder form), suitable for further dilution and/or mixing in water prior to application to the seed, plant, or locus. Alternatively, they can be provided as a ready-to-use solution or suspension for direct application. Because compositions disclosed and described herein can be combined with other AI's, such as fertilizer solutions and/or with pesticide solutions, they can be diluted and/or reconstituted by mixing with such other solutions. The above concentrate compositions are suitable for further dilution.

Seed, Foliage, and Locus Treatments or Coatings

Compositions disclosed and described herein can be applied using any conventional system for applying liquids to foliage, seed, or locus. Most commonly, application is by tumbling the seed with a liquid or powder form of the composition, which can be introduced to the seed by spraying will be found most convenient. For spraying, any conventional atomization method can be used to generate spray droplets, including hydraulic nozzles and rotating disk atomizers combined with the tumbler.

In one aspect, methods of promoting healthy growth of plant seeds is provided that comprises contacting the seeds with an aqueous composition comprising the first component, at least one agriculturally acceptable microorganism, and an optional component selected from one or more pesticides and/or one or more natural plant hormones. The seeds may be contacted with the composition by conventional means such as spraying, rolling, or tumbling in a continuous or batch-treating process. Thus, the first component can be combined with the at least one agriculturally acceptable microorganism and an optional component. Combinations of the first component and the at least one agriculturally acceptable microorganism can be mixed in aqueous media at a concentration, and brought into contact with the seeds for a time sufficient to provide improved plant health and/or growth.

For seed treatment or seed coatings, the amount of the first component can be about 0.01 mg/kg seed weight to about 10 mg/kg seed weight. Other concentrations of the compositions disclosed herein can be used.

For foliage surface or locus applications, the application rate of the compositions disclosed herein can be between about 0.01 gram/hectare to about 10.0 gram/hectare dry weight, between about 0.2 gram/hectare to about 2.0 gram/hectare dry weight, between 0.3 gram/hectare to about 1.5 gram/hectare dry weight, or between about 0.4 gram/hectare to about 1.0 gram/hectare dry weight applied in the soil or as a foliar application to the foliage or the locus of the plant. Other concentrations of the compositions disclosed herein can be used. In one aspect, absorption of the applied composition typically occurs at the site of application on a foliar surface, but the applied composition can run down to other areas and be absorbed there. Runoff (where an applied solution is shed from foliar surfaces and reaches the soil or other growing medium of the plant) is generally undesirable, but the applied nutrient is generally not totally lost as it can be absorbed by the plant's root system anytime during the expected life of the plant. However, methods of application that minimize runoff are preferred, and are well known to those of skill in the art.

Application solutions prepared by diluting concentrate compositions as described above represent further aspects of the compositions and methods disclosed and described herein.

For seed treatment applications, a concentrate composition can be diluted up to about 600-fold or more with water, more typically up to about 100-fold or up to about 40-fold. Illustratively, a concentrate product can be applied at about 0.01 mg/Kg seed to about 10 mg/Kg seed, for example about 0.1 mg/Kg seed, 0.5 mg/Kg seed, 2.5 mg/Kg seed or a higher amount. Other concentrations of the compositions disclosed herein can be used.

For application to plant foliage, a concentrate composition can be diluted up to about 600-fold or more with water, more typically up to about 100-fold or up to about 40-fold. Illustratively, a concentrate product can be applied at about 0.1 to about 30 l/ha, for example about 5 to about 25 l/ha, in a total application volume after dilution of about 60 to about 600 l/ha, for example about 80 to about 400 l/ha or about 100 to about 200 l/ha. Other concentrations of the concentrate compositions disclosed herein can be used For seed treatment applications, a concentrate composition can be diluted up to about 600-fold or more with water, more typically up to about 100-fold or up to about 40-fold. Illustratively, a concentrate product can be applied at about 0.1 mg/Kg seed to about 100 mg/Kg seed, for example about 0.1 mg/Kg seed, 1 mg/Kg seed, 10 mg/Kg seed. Other concentrations of the concentrate compositions disclosed herein can be used The compositions disclosed herein can be applied in a sequential order, for example, the seeds of a plant can be contacted with the first component, at least one microoganism and optionally at least one pesticide and the post-emergent plant or its locus can be contacted with the first component at least one microorganism and optionally at least one pesticide. The frequency of a foliar application of the compositions disclosed and described herein can be varied depending on many factors. It may be advantageous to apply a relatively high "starter" rate, followed by one or more subsequent applications at a lower rate. Application frequency can be, for example, a single application up to three applications per season. In certain situations, a single application will suffice. In other situations, the first and/or second and/or third application may precede, supersede, or correspond to a particular growth cycle of the plant, or a known life cycle or endemic habit of an insect, parasite, fungus, or undesirable plant species.

In another aspect, methods of promoting healthy growth of plant seeds is provided that comprises applying to the seeds a coating or dressing of a polymer or other matrix, the polymer or matrix comprising the first component and the at least one agriculturally acceptable microorganism, optionally one or more pesticides and/or one or more natural plant hormones. The polymer or matrix is capable of releasing the first component and the at least one agriculturally acceptable microorganism, optionally one or more pesticides and/or one or more natural plant hormones (collectively, "the actives"). The polymer or matrix can be designed to release the actives in response to temperature, moisture content, sunlight, time, or combinations thereof. The polymer or matrix can quickly dissolve or disintegrate releasing the actives or can controllable release the actives over time or in response to a predetermined condition such as temperature, moisture content, sunlight, time, or combinations thereof. The polymer or matrix can be multi-layer, with discrete layers, for example, for disrupting the coating to allow moisture ingress, housing the actives, etc. Suitable polymers or matrixes include hydrogels, microgels, or sol-gels. Specific materials and methods of coatings seeds useful in this regard include such process and materials as used, for example, Intellicoat™ (Landec Inc., Indiana); ThermoSeed™ (Incotec, Netherlands) CelPril™ Poncho™, Poncho/VOTiVo™ (Bayer CropScience); Apron-Maxx™ (Syngenta); and Nacret™ (Syngenta). The actives can be provided as nanoparticles and incorporated into the polymer or matrix, or directly adhered to the seed coat. The thickness of the polymer or matrix coating may be between from about 0.01 mils to about 10 mils in thickness. The coating can further provide protection for the seeds from mechanical and environmental damages and can facilitate the drilling process.

For seed treatment or seed coatings as described above, the amount of the first component can be about 0.01 mg/kg seed weight to about 10 mg/kg seed weight, however, higher rates can be employed.

Compositions for Seed Nodulation, Germination, Emergence, and Growth

Methods as described in detail above are useful for general nutrition and/or improved agronomical benefit of a plant seed. Any benefit related to enhanced nodulation, germination, emergence, and growth can be an agronomical benefit of the present methods, including without limitation improved root development (e.g., improved root or root hair growth), higher quality produce, improved growth and/or a longer growing season (which in either case can lead to higher yield of produce), faster emergence, improved plant stress management including increased stress tolerance and/or improved recovery from stress, increased mechanical strength, improved drought resistance, and improved plant health. Combinations of any of these benefits can be obtained.

In various embodiments, improved nodulation of seeds was observed and in addition, improved nodulation of seeds under stress conditions was observed from seeds treated with the compositions disclosed and described herein. Moreover, health and vigor recovery from a stress of the germinated seed treated with the compositions disclosed and described herein compared to seeds not so treated was improved.

Improved seed nodulation, germination, root development, emergence, and health, particularly resistance to or protection from disease, especially bacterial or fungal disease, is an important benefit of methods disclosed and described herein. In one embodiment, a method is provided for reducing susceptibility of a plant to insect, fungal or bacterial disease. "Reduced susceptibility" herein includes reduced incidence of fungal or bacterial infection and/or reduced impact of such infection as occurs on the health and growth of the plant. It is believed, without being bound by theory, that the enhanced nutrition afforded by compositions disclosed and described herein strengthens the plant's natural defenses against fungal and bacterial pathogens. Examples of such pathogens include, without limitation, *Alternaria* spp., *Blumeria graminis, Bottytis cinerea, Cochliobolus miyabeanus, Colletotrichum gloeosporioides, Diplocarpon rosae, Fusarium graminearum, Fusarium oxysporum, Magnaporthe grisea, Magnaporthe salvinii, Phaeosphaeria nodorum, Phoma lingam, Phomopsis* spp, *Pythium aphanidermatum, Pythium ultimum, Rhizoctonia solani, Sclerotinia homoeocarpa, Septoria nodorum, Sphaerotheca pannosa, Sphaerotheca xanthii, Thanatephorus cucumeris* and *Uncinula necator.*

A single species of pathogen can cause a variety of different diseases in different crops. Examples of bacterial and fungal diseases of plants include, without limitation, anthracnose, armillaria, ascochyta, aspergillus, bacterial blight, bacterial canker, bacterial speck, bacterial spot, bacterial wilt, bitter rot, black leaf, blackleg, black rot, black spot, blast, blight, blue mold, botrytis, brown rot, brown spot, cercospora, charcoal rot, cladosporium, clubroot, covered smut, crater rot, crown rot, damping off, dollar spot, downy mildew, early blight, ergot, erwinia, false loose smut, fire blight, foot rot, fruit blotch, fusarium, gray leaf spot, gray mold, heart rot, late blight, leaf blight, leaf blotch, leaf curl, leaf mold, leaf rust, leaf spot, mildew, necrosis, peronospora, phoma, pink mold, powdery mildew, rhizopus, root canker, root rot, rust, scab, smut, southern blight, stem canker, stem rot, verticillium, white mold, wildfire and yellows.

EXPERIMENTAL EXAMPLES

Experiment 1—Enhanced Seed Germination.

Three different crops (corn, soybean, and canola) were evaluated. In each experiment, 50 seeds were placed on sponges which had been soaked with 500 ml of water (the Control) or with 500 ml water that contained varying amounts of the first component. The first component concentrations varied from 0.6 mg a.i./Kg solution to 12 mg a.i./Kg. After seeds were placed on the sponges, they were placed in a dark growth chamber at 22° C. and the number of seeds which had germinated was determined every 24 hours until 90% of the seed had germinated or 120 hours, whichever came first. Germination results are shown in Tables 1-3.

TABLE 1

Canola Germination of control verses contact with first component.

| Treatment | Time (hours) | | | | |
|---|---|---|---|---|---|
| | 24 | 48 | 72 | 96 | 120 |
| Control | 0% | 7% | 20 | 35 | 47 |
| 0.6 mg/Kg | 0% | 9 | 38 | 75 | 77 |
| 1.2 mg/Kg | 0% | 11 | 36 | 60 | 66 |
| 6.0 mg/Kg | 0% | 11 | 24 | 69 | 71 |
| 12.0 mg/Kg | 0% | 12 | 32 | 51 | 58 |

TABLE 2

Soybean Germination of control verses contact with first component.

| Treatment | Time (hours) | | | | |
|---|---|---|---|---|---|
| | 24 | 48 | 72 | 96 | 120 |
| Control | 0% | 0% | 4% | 18% | 81% |
| 0.6 mg/Kg | 0% | 0% | 24% | 44% | 90% |
| 1.2 mg/Kg | 0% | 0% | 24% | 46% | 96% |
| 6.0 mg/Kg | 0% | 0% | 17% | 40% | 93% |
| 12.0 mg/Kg | 0% | 0% | 16% | 38% | 96% |

TABLE 3

Corn Germination of control verses contact with first component.

| | Time (hours) | | | | |
|---|---|---|---|---|---|
| Treatment | 24 | 48 | 72 | 96 | 120 |
| Control | 0% | 0% | 4% | 18% | 81% |
| 0.6 mg/Kg | 0% | 0% | 5% | 65% | 100% |
| 1.2 mg/Kg | 0% | 0% | 10% | 60% | 95% |
| 6.0 mg/Kg | 0% | 0% | 10% | 65% | 95% |
| 12.0 mg/Kg | 0% | 0% | 20% | 70% | 95% |

The results demonstrate the enhanced germination rate of a variety of crop seeds after contacting with the first component.

Experiment 2—Comparative Examples

A seed treatment product (STP) consisting of an NPK fertilizer (11-11-7) with 0.08% Zn, and 0.036% Gibberellic Acid was evaluated for emergence response in soybean seed, and compared with a control and a commercial seed treatment product, ApronMaxx (Syngenta). A fourth treatment sample consisted of a combination of STP and ApronMaxx. Seed was treated with 2 fl. oz. of seed treatment product per 100 pounds of seed and the seed were planted in pots and placed in a greenhouse. There were 6 replicates per treatment. Treatments were evaluated at 4 and 5 days after planting (DAP). Results are shown in Table 4. Emergence was rated as follows: N-No emergence—0 points; C-Crook, just breaking soil surface—1 point; E-Fully emerged—2 points.

TABLE 4

Emergence data for comparative examples

| | Average Rating Time | | | |
|---|---|---|---|---|
| Treatment | 5 DAP | | 6 DAP | |
| Control | 0.356 | b | 0.960 | b |
| STP | 1.306 | a | 1.720 | a |
| ApronMaxx | 0.444 | b | 0.960 | b |
| ApronMaxx + STP | 1.378 | a | 1.710 | a |

Means within columns and borders followed by the same letter Protected LSD are not different at the 5% level of significance (unless noted otherwise) as tested by Fishers Protected LSD.

This experiment demonstrates the effect of STP in speeding up germination and emergence of soybean seeds, compared to the Control and to ApronMaxx. It also shows that when STP was added to ApronMaxx, the emergence was nearly identical to the STP alone and significantly better than the Control or ApronMaxx alone.

Experiment 3—First Component Verses Comparative Example and Synergistic Combination of the First Component and Comparative Example In an experiment with soybean seed, the first component was compared to STP from Experiment 2 and with a combination of the first component and STP to determine the effect upon rate of germination. This trial was conducted using soybean seed treated with the first component alone, STP alone, or a combination of the first component and STP. In this experiment, 50 seeds were placed on sponges which had been soaked with 500 ml of water (the Control) or with 500 ml water that contained varying amounts of the first component or the first component plus STP. Germination was measured after 48, 72, and 120 hours. Results are shown in Table 5.

TABLE 5

Soybean emergence results with the first component ("CP") and STP

| | % Emerged Time | | | |
|---|---|---|---|---|
| Treatment | 24 hr | 48 hr | 72 hr | 96 hr |
| Control | 0% | 4% | 18% | 81% |
| 0.6 mg/Kg CP + .03% STP | 0% | 3% | 30% | 81% |
| 1.2 mg/Kg CP + .03% STP | 0% | 15% | 26% | 92% |
| 0.6 mg/Kg CP | 0% | 24% | 44% | 90% |
| 1.2 mg/Kg CP | 0% | 24% | 46% | 96% |

This experiment demonstrates that the first component alone at either 0.6 mg/Kg or 1.2 mg/Kg rate causes the germination rate to increase faster than the control or the STP plus the first component. 1.2 mg/Kg of first component added to the STP improved performance significantly over the 0.6 mg/Kg of the first component added to the STP. However, when the same experiment was repeated for corn, the results showed the opposite effect. Here, both treatments alone improved germination versus the control, but adding STP to each treatment with the first component resulted in a further enhancement in the germination rates as seen in Table 6.

TABLE 6

Corn emergence results with the first component (CP) and STP.

| | % Emerged Time | | |
|---|---|---|---|
| Treatment | 72 hr | 96 hr | 120 hr |
| Control | 0% | 50% | 95% |
| 0.6 mg/Kg CP + .03% STP | 10% | 60% | 95% |
| 1.2 mg/Kg CP + .03% STP | 15% | 90% | 100% |
| 0.6 mg/Kg CP | 5% | 65% | 100% |
| 1.2 mg/Kg CP | 10% | 60% | 95% |

In the case of corn, the first component alone improves germination, but there is an additive effect or synergistic effect when the STP is added to the first component as demonstrated by the above experimental data.

Experiment 4—Combination of First Component and Microorganism for Improved Nodulation The purpose of this experiment was to determine if treating inoculated (*Bradyrhzobium japonicum*) soybean (*Glycine max.*) seeds with CP would increase or decrease nodulation under non stressed growing conditions. A field trial was conducted and consisted of 5 treatments with 4 replications per treatment in a Randomized Complete Block design.

Seeds were pretreated with a "pre-inoculant" of *B. japonicum* that was indicated to have an extended shelf life of 21 to 30 days. Prior to planting, the inoculated seeds were treated with CP at four different rates ranging from 0.062 mg CP/kg of seed to 7.75 mg CP/kg of seed. One batch of seed was not treated with CP and was the untreated check (UTC). Plants were harvested 25 days after planting to count nodules per plant. Results are shown in FIG. 1. Results statistically significant at p=0.05. This experiment demonstrates that CP increases the nodulation of soybean plants when applied with inoculants containing *B. japonicium*.

Experiment 5—Combination of First Component and Microorganism for Improved Nodulation Under Stress Conditions The purpose of this experiment was to determine if treating inoculated (*Bradyrhzobium japonicum*) soybean (*Glycine*

Figure 2:
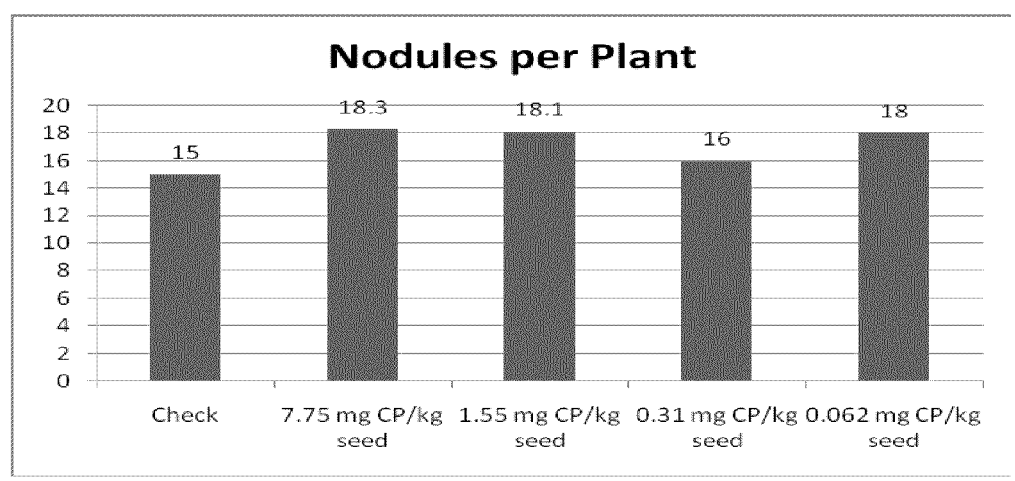
FIG. 2. graphically depicts experimental results of testing aspects of the embodiments disclosed herein.

*max.*) seeds with CP would increase or decrease nodulation under stressed growing conditions. Thus, a field trial was conducted and consisted of 5 treatments with 4 replications per treatment in a Randomized Complete Block design. Seeds were pretreated with a "pre-inoculant" of *B. japonicum* was indicated to have an extended shelf life of 21 to 30 days. Prior to planting, the inoculated seeds were treated with CP at four different rates ranging from 0.062 mg CP/kg of seed to 7.75 mg CP/kg of seed. One batch of seed was not treated with CP and was the untreated check (UTC). Seed was planted and immediately following planting, the seed beds were irrigated until they were completely water saturated. Plants were harvested 25 days later to count nodules per plant. Results are shown in FIG. 2. This experiment demonstrates that CP increases the nodulation of soybean plants when applied with inoculants containing *B. japonicium*.

Experiment 6—Combination of First Component and Microorganism for Improved Emergence & Under Stress Conditions The purpose of this experiment was to determine if treating inoculated (*Bradyrhzobium japonicum*) soybean (*Glycine max.*) seeds with CP would impact plant emergence and final population under stressed growing conditions. Thus, a field trial was conducted and consisted of 5 treatments with 4 replications per treatment in a Randomized Complete Block design.

Figure 3:
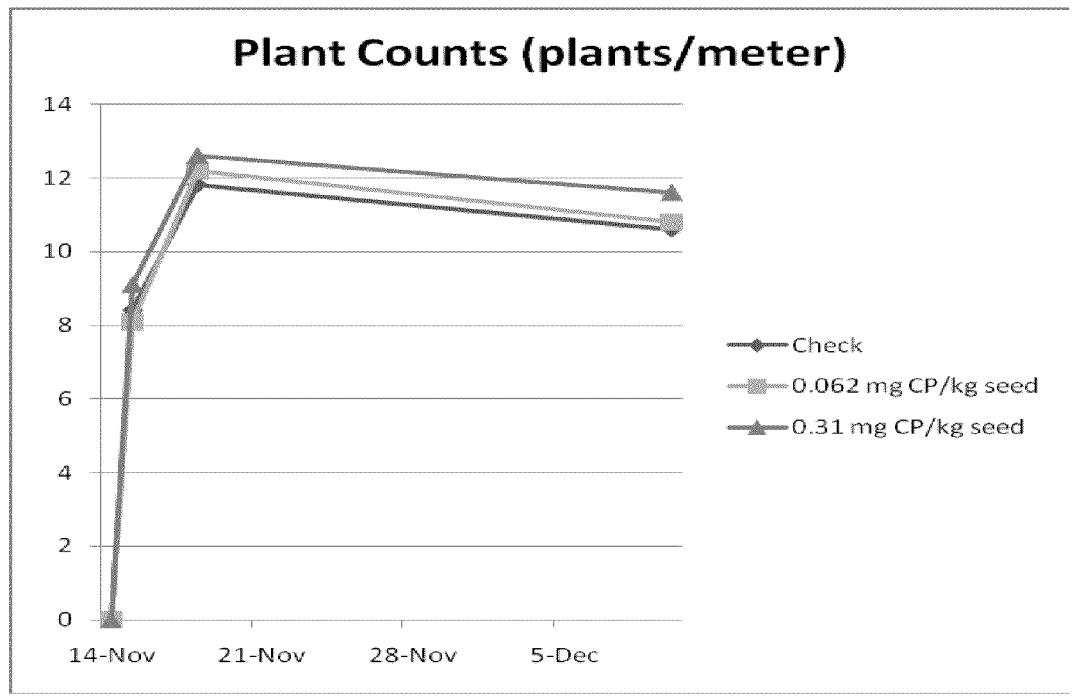
FIG. 3. graphically depicts experimental results of testing aspects of the embodiments disclosed herein.

Seeds were pretreated with a "pre-inoculant" of *B. japonicum* was indicated to have an extended shelf life of 21 to 30 days. Prior to planting, the inoculated seeds were treated with CP at two different rates of 0.062 mg CP/kg of seed and 0.31 mg CP/kg of seed. One batch of seed was not treated with CP and was the untreated check (UTC). Seed was planted on Day 1, and immediately following planting, the seed beds were irrigated until they were completely water saturated. Plant counts were made on Day 2 and Day 4 with a final plant count on Day 25. Results were measured in plants per meter of row and are shown in FIG. 3. This experiment demonstrates that when CP is applied to inoculated soybean seed prior to planting, it has a positive effect on emergence and final plant populations.

Figure 4:
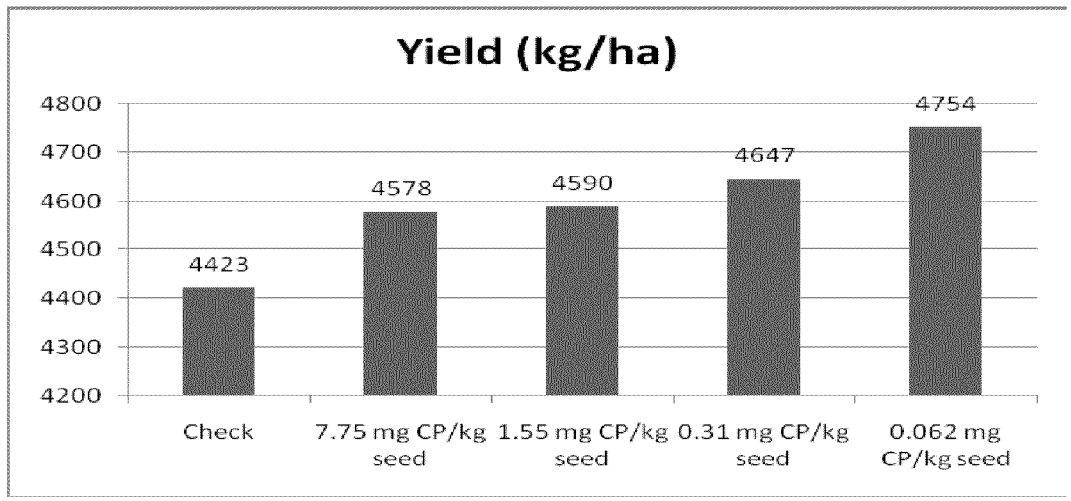
FIG. 4. graphically depicts experimental results of testing aspects of the embodiments disclosed herein.

Experiment 7—Combination of First Component and Microorganism for Improved Yield The purpose of this experiment was to determine if treating inoculated (*Bradyrhzobium japonicum*) soybean (*Glycine max.*) seeds with CP would increase or decrease yield. Thus, a field trial was conducted and consisted of 5 treatments with 4 replications per treatment in a Randomized Complete Block design. Seeds were pretreated with a "pre-inoculant" of *B. japonicum* that was indicated to have an extended shelf life of 21 to 30 days. Prior to planting, the inoculated seeds were treated with CP at four different rates ranging from 0.062 mg CP/kg of seed to 7.75 mg CP/kg of seed. One batch of seed was not treated with CP and was the untreated check (UTC). Seed was planted and the plots were harvested approximately 148 days later to determine final yields. Results are shown in FIG. 4. This experiment demonstrated that the addition of CP to inoculated soybean seeds increased the final yield by as much as 7.5%, and averaged 4.96% across all treatments.

Combination of First Component and Microorganism for GM Seed

In planta, metabolism is generally unpredictable, i.e., one cannot predict from prior uses of the first component, a microorganism, and optionally a pesticide, what beneficial agronomical effects may result, especially for genetically modified (GM) plants. For example, contact of a GM crop would benefit from the compositions and methods disclosed and described herein as the first component will regulate one or more genes of the GM crop and as a result, it is generally believed that the compositions and methods would effectively provide one or more of the following:

a. decrease in one or both of the levels normally used for the microorganism/optional pesticide than possible without the first component in one or more GM crops;

b. increased resistance of one or more GM crops against biotic (e.g., insects, fungi, viruses, nematodes, and other pathogens) and abiotic stresses (e.g., drought, cold, salinity, ozone, soil nutrient deficiencies), with resulting increases in yields and improved quality of such crops;

c. increase the nodulation, emergence, root development and overall vigor of one or more GM crops.

d. increase the absorption of multivalent metal ions in one or more GM crops.

It is generally believed that the benefits of the methods and compositions herein disclosed and described would be useful for many other GM crops and may further be applicable to the development and testing of such GM crops.

Thus, a method for increasing the germination rate of a seed, is contemplated, comprising contacting a GM seed with the first component and at least one microorganism, optionally with a pesticide in an amount that improves the germination, emergence, root development or vigor of the GM seed as compared to a seed of the same genotype not contacted with the composition disclosed herein.

All patents and publications cited herein are incorporated by reference into this application in their entirety.

The words "comprise", "comprises", and "comprising" are to be interpreted inclusively rather than exclusively.

What is claimed is:

1. A seed composition comprising:
   a seed;
   a first component comprising an agriculturally acceptable complex mixture of dissolved organic material comprising natural organic matter that is two or more of:
   (i) a mixture of condensed hydrocarbons, lignins, and tannins and/or condensed tannins;
   (ii) a oxygen-to-carbon ratio for the dissolved organic matter of greater than about 0.5;
   (iii) a total number of tannin compounds greater than about 200, the tannin compounds having a hydrogen to carbon ration of about 0.5 to about 1.4, and an aromaticity index of less than about 0.7 as measured by mass spectroscopy; or
   (iv) a mass distribution of about 47-56% lignin compounds, 33-42% tannin compounds, and about 8-11% condensed hydrocarbon as measured by mass spectroscopy and
   at least one agriculturally acceptable microorganism.

2. The seed composition of claim 1, wherein the first component is characterized by comprising a mixture of condensed hydrocarbons, lignins, and tannins and/or condensed tannins, characterized in that at least 10% of the total % of compounds of the composition are tannins and/or condensed tannins.

3. The seed composition of claim 1, wherein the first component is characterized by comprising a mixture of condensed hydrocarbons, lignins, and tannins and/or condensed tannins, characterized in that at least 20% of the total % of compounds of the composition are tannins and/or condensed tannins.

4. The seed composition of claim 1, wherein the at least one agriculturally acceptable microorganism is at least one of an inoculant, pre-inoculant, and trans-inoculant.

5. The seed composition of claim 4, wherein the microorganism is at least one of a nitrogen-fixing bacteria, a phosphate-solubilizing bacteria, a fungal inoculants, and a composite inoculant.

6. The seed composition of claim 4, wherein the microorganism is at least one from the species *Rhizobium, Brandyrhizobium, Bacillus, Azobacter, Arhrobacter, Pseudomonas, Azospirillium, cyanobacteria*, and *mycorrihizal fungae*.

7. The seed composition of claim 1, further comprising at least one of a herbicide, an insecticide, a fungicide, a bactericide, an anti-viral, a plant nutrient, or a combination thereof.

8. The seed composition of claim 7, wherein the first component and the at least one of a herbicide, an insecticide, a fungicide, a bactericide, an anti-viral, a plant nutrient, or a combination thereof are releasably contained in a polymer matrix contacting the seed.

9. The seed composition of claim 8, wherein the at least one microorganism is deposited on the polymer matrix contacting the seed.

10. A method of seed treating, the method comprising contacting a seed with a first component comprising an agriculturally acceptable complex mixture of dissolved organic material characterized by natural organic matter that is two or more of:
   (i) a mixture of condensed hydrocarbons, lignins, and tannins and/or condensed tannins;
   (ii) a oxygen-to-carbon ratio for the dissolved organic matter of greater than about 0.5;
   (iii) a total number of tannin compounds greater than about 200, the tannin compounds having a hydrogen to carbon ration of about 0.5 to about 1.4, and an aromaticity index of less than about 0.7 as measured by mass spectroscopy; or
   (iv) a mass distribution of about 47-56% lignin compounds, 33-42% tannin compounds, and about 8-11% condensed hydrocarbon as measured by mass spectroscopy; and a second component of at least one agriculturally acceptable microorganism.

11. The method of claim 10, wherein the first component is characterized by comprising a mixture of condensed hydrocarbons, lignins, and tannins and/or condensed tannins, characterized in that at least 10% of the total % of compounds of the composition are tannins and/or condensed tannins.

12. The method of claim 10, wherein the first component is characterized by comprising a mixture of condensed hydrocarbons, lignins, and tannins and/or condensed tannins, characterized in that at least 20% of the total % of compounds of the composition are tannins and/or condensed tannins.

13. The method of claim 10, wherein the at least one agriculturally acceptable microorganism is at least one of an inoculant, pre-inoculant, and trans-inoculant.

14. The method of claim 13, wherein the inoculant, pre-inoculant, or trans-inoculant is at least one from the species *Rhizobium, Brandyrhizobium, Bacillus, Azobacter, Arhrobacter, Pseudomonas, Azospirillium, cyanobacteria*, and *mycorrihizal fungae*.

15. The method of claim 10, further comprising contacting the seed with at least one pesticide, with the proviso that the fungicide, bactericide, and anti-viral are agronomically ineffective against the at least one microorganism, wherein the pesticide comprises at least one of a herbicide, an insecticide, a fungicide, a bactericide, an anti-viral, and a plant nutrient.

16. The method of claim 15, wherein seed is contacted with the first component, and the at least one pesticide, followed by contacting with the at least one agriculturally acceptable microorganism, and a polymer matrix.

17. The method of claim 16, wherein the first component and the pesticide are contained in a polymer matrix contacting at least a portion of the seed, and at least a portion of the polymer matrix is contacted with the at least one microorganism.

18. The method of claim 16, wherein the first component or the at least one pesticide is controllably released from the polymer matrix.

19. A method comprising
contacting a seed, foliar surface, or locus of a plant with a composition comprising a first component comprising an agriculturally acceptable complex mixture of dissolved organic material comprising natural organic matter that is two or more of:
   (i) a mixture of condensed hydrocarbons, lignins, and tannins and/or condensed tannins;
   (ii) a oxygen-to-carbon ratio for the dissolved organic matter of greater than about 0.5;
   (iii) a total number of tannin compounds greater than about 200, the tannin compounds having a hydrogen to carbon ration of about 0.5 to about 1.4, and an aromaticity index of less than about 0.7 as measured by mass spectroscopy; or
   (iv) a mass distribution of about 47-56% lignin compounds, 33-42% tannin compounds, and about 8-11% condensed hydrocarbon as measured by mass spectroscopy; and at least one agriculturally acceptable microorganism;
wherein the composition enhances one or more of nodulation, germination, emergence, root development, seedling vigor, seedling growth, activity of the inoculant, or nutrient uptake compared to the seed not contacted with the first component or the at least one agriculturally acceptable microorganism.

20. The method of claim 19, wherein the first component is characterized by comprising a mixture of condensed hydrocarbons, lignins, and tannins and/or condensed tannins, characterized in that at least 10% of the total % of compounds of the composition are tannins and/or condensed tannins.

21. The method of claim 19, wherein the first component is characterized by comprising a mixture of condensed hydrocarbons, lignins, and tannins and/or condensed tannins, characterized in that at least 20% of the total % of compounds of the composition are tannins and/or condensed tannins.

22. The method of claim 19, further comprising contacting the seed with at least one pesticide, with the proviso that the fungicide, bactericide, and anti-viral are agronomically ineffective against the at least one microorganism, wherein the pesticide comprises at least one of a herbicide, an insecticide, a fungicide, a bactericide, an anti-viral, and a plant nutrient.

23. The method of claim 22, wherein the pesticide is an insecticide, a fungicide, bactericide, anti-viral, or combinations thereof.

24. The method of claim 22, wherein seed is contacted with the first component and the at least one pesticide followed by the microorganism.

25. The method of claim 22, wherein seed is contacted with the first component, the at least one microorganism, and the pesticide essentially simultaneously.

26. The method of claim 24, wherein the polymer or matrix contacting the seed further comprises the at least one agriculturally acceptable microorganism.

27. The method of claim 19, where the plant or the seed is of a legume crop, a fruit, or a vegetable crop.

28. The method of claim 19, wherein the plant or the seed is genetically modified.

29. A plant nutrient composition comprising:
a first component comprising concentrated, aqueously dissolved organic material; wherein the first component is characterized by two or more of:
(i) a mixture of condensed hydrocarbons, lignins, and tannins and/or condensed tannins;
(ii) a oxygen-to-carbon ratio for the dissolved organic matter of greater than about 0.5;
(iii) a total number of tannin compounds greater than about 200, the tannin compounds having a hydrogen to carbon ration of about 0.5 to about 1.4, and an aromaticity index of less than about 0.7 as measured by mass spectroscopy; or
(iv) a mass distribution of about 47-56% lignin compounds, 33-42% tannin compounds, and about 8-11% condensed hydrocarbon as measured by mass spectroscopy and
at least one agriculturally acceptable microorganism.

30. The plant nutrient composition of claim 29, wherein the first component is characterized by comprising a mixture of condensed hydrocarbons, lignins, and tannins and/or condensed tannins, characterized in that at least 10% of the total % of compounds of the composition are tannins and/or condensed tannins.

31. The plant nutrient composition of claim 29, wherein the first component is characterized by comprising a mixture of condensed hydrocarbons, lignins, and tannins and/or condensed tannins, characterized in that at least 20% of the total % of compounds of the composition are tannins and/or condensed tannins.

* * * * *